US010315041B2

(12) United States Patent
Riehl et al.

(10) Patent No.: US 10,315,041 B2
(45) Date of Patent: Jun. 11, 2019

(54) FERROFLUIDIC COOLING AND ACOUSTICAL NOISE REDUCTION IN MAGNETIC STIMULATORS

(75) Inventors: Mark Edward Riehl, Doylestown, PA (US); Kenneth Ghiron, Allentown, PA (US)

(73) Assignee: Neuronetics, Inc., Malvern, PA (US)

( * ) Notice: Subject to any disclaimer, the term of this patent is extended or adjusted under 35 U.S.C. 154(b) by 1779 days.

(21) Appl. No.: 12/018,840

(22) Filed: Jan. 24, 2008

(65) Prior Publication Data

US 2008/0177128 A1 Jul. 24, 2008

Related U.S. Application Data

(63) Continuation of application No. 11/130,657, filed on May 17, 2005, now Pat. No. 7,396,326.

(51) Int. Cl.
| A61N 1/00 | (2006.01) |
| A61N 2/00 | (2006.01) |
| F28D 21/00 | (2006.01) |
| H01F 7/20 | (2006.01) |
| H01F 27/10 | (2006.01) |

(52) U.S. Cl.
CPC ...... *A61N 2/006* (2013.01); *F28D 2021/0029* (2013.01); *H01F 7/202* (2013.01); *H01F 27/105* (2013.01)

(58) Field of Classification Search
CPC . A61N 2/006; F28D 2021/0029; H01F 7/202; H01F 27/105
USPC ......... 600/13, 9; 128/897–899; 335/300, 62; 310/52; 417/50; 165/58
See application file for complete search history.

(56) References Cited

U.S. PATENT DOCUMENTS

| 2,651,258 | A | * | 9/1953 | Pierce | H01J 7/186 |
| | | | | | 137/251.1 |
| 3,287,677 | A | * | 11/1966 | Mohr | H01F 27/08 |
| | | | | | 310/11 |
| 3,658,051 | A | | 4/1972 | Maclean | 600/14 |
| 3,683,923 | A | | 8/1972 | Anderson | 128/303.14 |
| 4,078,392 | A | | 3/1978 | Kestner | 62/99 |
| 4,473,074 | A | | 9/1984 | Vassiliadis | |
| 4,601,753 | A | | 7/1986 | Soileau et al. | 75/251 |

(Continued)

FOREIGN PATENT DOCUMENTS

| EP | 0998958 A2 | 5/2000 |
| EP | 1273320 A1 | 1/2003 |

(Continued)

OTHER PUBLICATIONS

WO 2003/084605 A1, Official Action dated Dec. 27, 2010 issued in related Japanese Application No. 2007-508573.

(Continued)

*Primary Examiner* — Navin Natnithithadha
*Assistant Examiner* — Sunita Reddy
(74) *Attorney, Agent, or Firm* — Condo Roccia Koptiw LLP

(57) ABSTRACT

A ferrofluid chamber has a housing that is adapted to be coupled to a component that generates a magnetic field. The housing may be disposed around the component so as to insulate a noise-producing region of the component. The magnetic field may be of sufficient strength to stimulate anatomical tissue. In addition, a ferrofluid may be disposed within the housing for cooling the component.

36 Claims, 6 Drawing Sheets

(56) References Cited

U.S. PATENT DOCUMENTS

| | | |
|---|---|---|
| 4,638,798 A | 1/1987 | Shelden et al. |
| 4,712,558 A | 12/1987 | Kidd et al. |
| 4,808,079 A * | 2/1989 | Crowley ............... F04B 17/00 310/11 |
| 4,940,453 A | 7/1990 | Cadwell |
| 4,994,015 A | 2/1991 | Cadwell ........................ 600/13 |
| 4,995,395 A | 2/1991 | Ilmoniemi et al. |
| 5,005,639 A | 4/1991 | Leland |
| 5,047,005 A | 9/1991 | Cadwell |
| 5,061,234 A | 10/1991 | Chaney |
| 5,066,272 A | 11/1991 | Eaton et al. |
| 5,078,674 A | 1/1992 | Cadwell ........................ 600/13 |
| 5,097,833 A | 3/1992 | Campos ....................... 128/421 |
| 5,116,304 A | 5/1992 | Cadwell ........................ 600/13 |
| 5,254,123 A | 10/1993 | Bushey |
| 5,299,569 A | 4/1994 | Wernicke et al. ............. 607/45 |
| 5,462,685 A * | 10/1995 | Raj ........................ H01F 1/44 174/15.1 |
| 5,655,534 A | 8/1997 | Ilmoniemi |
| 5,707,334 A | 1/1998 | Young .............................. 600/9 |
| 5,725,471 A | 3/1998 | Davey et al. |
| 5,766,124 A | 6/1998 | Polson |
| 5,769,778 A | 6/1998 | Abrams et al. |
| 5,812,301 A | 9/1998 | Nakamura |
| 5,813,970 A | 9/1998 | Abrams et al. |
| 5,820,623 A | 10/1998 | Ng |
| 5,871,517 A | 2/1999 | Abrams et al. |
| 6,057,373 A | 5/2000 | Fogel |
| 6,066,084 A | 5/2000 | Edrich et al. |
| 6,074,385 A | 6/2000 | Klopotek ....................... 606/27 |
| 6,086,525 A | 7/2000 | Davey et al. |
| 6,117,066 A | 9/2000 | Abrams et al. |
| 6,155,966 A | 12/2000 | Parker |
| 6,169,963 B1 | 1/2001 | Markov |
| 6,179,769 B1 | 1/2001 | Ishikawa et al. .................. 600/9 |
| 6,179,770 B1 | 1/2001 | Mould |
| 6,179,771 B1 | 1/2001 | Mueller ........................ 600/13 |
| 6,198,958 B1 | 3/2001 | Ives et al. ..................... 600/411 |
| 6,210,317 B1 | 4/2001 | Bonlie |
| 6,223,750 B1 * | 5/2001 | Ishikawa et al. ............. 128/885 |
| 6,242,994 B1 * | 6/2001 | Li et al. ........................ 335/277 |
| 6,253,109 B1 | 6/2001 | Gielen |
| 6,256,531 B1 | 7/2001 | Ilmoniemi et al. ............. 600/544 |
| 6,266,556 B1 | 7/2001 | Ives et al. |
| 6,279,579 B1 | 8/2001 | Riaziat et al. |
| 6,366,814 B1 | 4/2002 | Boveja et al. |
| 6,389,318 B1 | 5/2002 | Zarinetchi et al. ............. 607/61 |
| 6,402,678 B1 | 6/2002 | Fischell et al. ................. 600/13 |
| 6,425,852 B1 | 7/2002 | Epstein et al. |
| 6,434,410 B1 | 8/2002 | Cordero et al. |
| 6,463,328 B1 | 10/2002 | John .............................. 607/45 |
| 6,480,743 B1 | 11/2002 | Kirkpatrick et al. ........... 607/45 |
| 6,484,059 B2 | 11/2002 | Gielen ........................... 607/45 |
| 6,488,617 B1 | 12/2002 | Katz |
| 6,497,648 B1 | 12/2002 | Rey ................................ 600/14 |
| 6,503,187 B1 | 1/2003 | Ilmoniemi et al. ............. 600/14 |
| 6,516,288 B2 | 2/2003 | Bagne ........................ 702/179 |
| 6,537,197 B1 | 3/2003 | Ruohonen et al. |
| 6,551,233 B2 | 4/2003 | Perreault et al. |
| 6,560,490 B2 | 5/2003 | Grill et al. ..................... 607/72 |
| 6,567,702 B1 | 5/2003 | Nekhendzy et al. ........... 607/46 |
| 6,571,123 B2 | 5/2003 | Ives et al. ..................... 600/544 |
| 6,572,528 B2 | 6/2003 | Rohan et al. |
| 6,591,138 B1 | 7/2003 | Fischell et al. |
| 6,629,935 B1 | 10/2003 | Miller et al. ................... 600/558 |
| 6,641,520 B2 | 11/2003 | Bailey et al. ..................... 600/9 |
| 6,663,556 B2 | 12/2003 | Barker .......................... 600/14 |
| 6,671,555 B2 | 12/2003 | Gielen et al. |
| 6,827,681 B2 | 12/2004 | Tanner et al. .................... 600/9 |
| 6,849,040 B2 | 2/2005 | Ruohonen et al. ............. 600/14 |
| 6,927,510 B1 * | 8/2005 | Beitelman et al. ............. 310/54 |
| 6,978,179 B1 | 12/2005 | Flagg et al. ................... 607/45 |
| 6,982,501 B1 | 1/2006 | Kotha et al. |
| 7,367,936 B2 | 5/2008 | Myers et al. |
| 7,396,326 B2 * | 7/2008 | Ghiron ................... A61N 2/006 600/13 |
| 7,745,962 B2 | 6/2010 | Morgenstein |
| 2001/0031906 A1 * | 10/2001 | Ishikawa ................ A61N 2/008 600/13 |
| 2002/0013612 A1 | 1/2002 | Whitehurst .................... 607/45 |
| 2002/0087201 A1 | 7/2002 | Firlik et al. .................... 607/45 |
| 2002/0091419 A1 | 7/2002 | Firlik et al. .................... 607/45 |
| 2002/0103515 A1 | 8/2002 | Davey et al. .................. 607/66 |
| 2002/0123780 A1 | 9/2002 | Grill et al. |
| 2002/0160436 A1 | 10/2002 | Markov et al. |
| 2002/0169355 A1 | 11/2002 | Rohan et al. |
| 2003/0004392 A1 | 1/2003 | Tanner et al. ..................... 600/9 |
| 2003/0023159 A1 | 1/2003 | Tanner ......................... 600/417 |
| 2003/0028072 A1 | 2/2003 | Fischell et al. ................. 600/13 |
| 2003/0050527 A1 | 3/2003 | Fox et al. ....................... 600/13 |
| 2003/0073899 A1 | 4/2003 | Ruohonen et al. ........... 600/417 |
| 2003/0074032 A1 | 4/2003 | Gliner |
| 2003/0082507 A1 | 5/2003 | Stypulkowski |
| 2003/0087264 A1 | 5/2003 | Kaplitt et al. |
| 2003/0088274 A1 | 5/2003 | Gliner et al. ..................... 607/3 |
| 2003/0097161 A1 | 5/2003 | Firlik et al. .................... 607/72 |
| 2003/0125786 A1 | 7/2003 | Gliner et al. ................. 607/116 |
| 2003/0130706 A1 | 7/2003 | Sheffield et al. ............... 607/46 |
| 2003/0195588 A1 | 10/2003 | Fischell et al. ................. 670/55 |
| 2003/0204135 A1 | 10/2003 | Bystritsky .................... 600/407 |
| 2004/0010177 A1 | 1/2004 | Rohan et al. ..................... 600/9 |
| 2004/0019370 A1 | 1/2004 | Gliner et al. |
| 2004/0051279 A1 | 3/2004 | Grant et al. |
| 2004/0077921 A1 | 4/2004 | Becker et al. ..................... 600/9 |
| 2004/0077923 A1 | 4/2004 | Frimerman et al. |
| 2004/0127942 A1 | 7/2004 | Yomtov et al. ................... 607/3 |
| 2004/0138524 A1 | 7/2004 | Ueda et al. |
| 2004/0138550 A1 | 7/2004 | Hartlep et al. |
| 2004/0138578 A1 | 7/2004 | Pineda et al. |
| 2004/0143300 A1 | 7/2004 | Rogers |
| 2004/0153129 A1 | 8/2004 | Pless et al. ..................... 607/62 |
| 2004/0172012 A1 | 9/2004 | Otsuka et al. |
| 2004/0193001 A1 | 9/2004 | Miller |
| 2004/0204625 A1 | 10/2004 | Riehl et al. |
| 2005/0021104 A1 | 1/2005 | DiLorenzo ..................... 607/45 |
| 2005/0124848 A1 | 6/2005 | Holzner ........................... 600/9 |
| 2005/0216071 A1 | 9/2005 | Devlin et al. ................... 607/48 |
| 2005/0228209 A1 | 10/2005 | Schneider et al. ............. 600/13 |
| 2005/0256539 A1 | 11/2005 | George et al. ................... 607/2 |
| 2006/0110260 A1 | 5/2006 | Hsu |

FOREIGN PATENT DOCUMENTS

| | | |
|---|---|---|
| JP | 1996-52231 A | 2/1996 |
| JP | 2001-509635 A | 7/2001 |
| JP | 2006-516480 A | 7/2006 |
| WO | WO 1996/016692 A | 6/1996 |
| WO | WO 1999/002467 A1 | 1/1999 |
| WO | WO 1999/055421 A2 | 11/1999 |
| WO | WO 1999/64884 A1 | 12/1999 |
| WO | WO 2000/074777 A1 | 12/2000 |
| WO | WO 2001/012236 A2 | 2/2001 |
| WO | WO 2001/028622 A2 | 4/2001 |
| WO | WO 2001/97906 A2 | 12/2001 |
| WO | WO 2002/09811 A1 | 2/2002 |
| WO | WO 2002/031604 A1 | 4/2002 |
| WO | WO 2002/032504 A2 | 4/2002 |
| WO | WO 2002/072194 A2 | 9/2002 |
| WO | WO 2002/085449 A2 | 10/2002 |
| WO | WO 2002/085454 A1 | 10/2002 |
| WO | WO 2002/089902 A2 | 11/2002 |
| WO | WO 2002/094997 A2 | 11/2002 |
| WO | WO 2003/035163 A2 | 5/2003 |
| WO | WO 2003/039468 A2 | 5/2003 |
| WO | WO 2003/082405 A1 | 10/2003 |
| WO | WO 2003/084605 A1 | 10/2003 |
| WO | WO 2003/085546 A1 | 10/2003 |
| WO | WO 2003/090604 A2 | 11/2003 |
| WO | WO 2003/098268 A1 | 11/2003 |
| WO | WO 2004/006750 A2 | 1/2004 |
| WO | WO 2004/018128 A2 | 3/2004 |
| WO | WO 2004/082759 A2 | 9/2004 |

(56) References Cited

FOREIGN PATENT DOCUMENTS

| WO | WO 2004/100765 A2 | 11/2004 |
|---|---|---|
| WO | WO 2005/000401 A1 | 1/2005 |
| WO | WO 2005/065768 A1 | 7/2005 |

OTHER PUBLICATIONS

WO 2003/085546 A1, Information Disclosure Statement filed on Jul. 24, 2008 in related U.S. Appl. No. 12/127,226.
2001-509635 A, WO 1999/02467.
2006-516480 A, WO 2004/018128 A2.
Awiszus et al., "Characterization of Paired-Pulse Transcranial Magnetic Stimulation Conditions Yielding Intracortical Inhibition of I-Wave Facilitation using a Threshold Paradigm", Experimental Brain Research, Nov. 1999, 129(2), 317-324.
Garcia-Toro et al., "Modest Adjunctive Benefit with Transcranial Magnetic Stimulation in Medication-Resistant Depression", Journal of Affective Disorders, May 2001, 64(2-3), 271-275.
George, M.S., "New Methods of Minimally Invasive Brain Modulation as Therapies in Psychiatry:TMS, MST, VNS and DBS", Chinese Medical Journal (Taipei), Aug. 2002, 65(8), 349-360.
Iramina et al., "Effects of Transcranial Magnetic Stimulation on EEG Activity", IEEE transactions on Magnetics, Sep. 2002, 38(5), 3347-3349.
Lisanby et al., "Magnetic Seizure Therapy of Major Depression", Arch. Gen. Psychiatry, Mar. 2001, 58, 303-307.
Lisanby, S.H., "Safety and Feasibility of Magnetic Seizure Therapy (MST) in Major Depression: Randomized Within-Subject Comparison with Electroconvulsive Therapy", Neuropsychopharmacology, New York State Psychiatric Institute, Jul. 2003, 28(10), 1852-1865.
Lisanby, S.H., "Update on Magnetic Seizure Therapy: A Novel Form of Convulsive Therapy", The Journal of ECT, Dec. 2002, 18(4), 182-188.
Pascual-Leone et al., "Rapid-Rate Transcranial Magnetic Stimulation of Left Dorsolateral Prefrontal Cortex in Drug-Resistant Depression", The Lancet, Jul. 27, 1996, 348(9022), 233-237.
Roth et al., "A Coil Design for Transcranial Magnetic Stimulation of Deep Brain Regions", Journal of Clinical Neurophysiology, Aug. 2002, 19(4), 361-370.
Sommer et al., "Increased Transcranial Magnetic Motor Threshold after ECT", European Archives of Psychiatry and Clinical Neuroscience, Oct. 2002, 252(5), 250-252.
Terrace et al., "The Cognitive Effects of Electroconvulsive Shock and Magnetic SeizureTherapy in Rhesus Monkeys", Society for Neuroscience Abstract Viewer and Itinerary Planner, Dec. 2002, Abstract Only # 536.7, 27(1), 1418.
Trivedi, M.H., "Treatment-Resistant Depression: New Therapies on the Horizon", Annals of Clinical Psychiatry, Mar. 2003, 15(1), 59-70.
Baudewig et al., "Functional MRI of Cortical Activations Induced by Transcranial Magnetic Stimulation (TMS)", Brain Imaging, Neuro Report, vol. 12, No. 16, Nov. 16, 2001, pp. 3543-3548.
Bohning et al., "A Combined TMS/fMRI Study of Intensity-Dependent TMS Over Motor Cortex", Priority Communication, Society of Biological Psychiatry, vol. 45, 1999, pp. 385-394.
Bohning et al., "A TMS Coil Positioning/Holding System for MR Image-Guided TMS Interleaved with fMRI", Clinical Neurophysiology, vol. 114, 2003, pp. 2210-2219.
Bohning et al., "Bold-fMRI Response to Single-Pulse Transcranial Magnetic Stimulation (TMS)", Journal of Magnetic Resonance Imaging, Wtley-Liss Inc., vol. 11, 2000, pp. 569-574.
George et al., "A Controlled Trial of Daily Left Prefrontal Cortex TMS for Treating Depression", Society of Biological Psychiatry, vol. 48, 2000, pp. 962-970.
Grafman, Jordan, "TMS as a Primary Brain Mapping Tool", Transcranial Magnetic Stimulation in Neuropsychiatry, 2000, pp. 115-140.
Hess et al., "Magnetic Stimulation of the Human Brain: Influence of Size and Shape of the Stimulating Coil", Motor Disturbances II, vol. 3, 1990, pp. 31-42.
Lisanby et al., "Sham TMS: Intracerebral Measurement of the Induced Electrical Field and the Induction of Motor-Evoked Potentials", Society of Biological Psychiatry, vol. 49, 2001, pp. 460-463.
Loo et al., "Transcranial Magnetic Stimulation (TMS) in Controlled Treatment Studies: Are Some "Sham" Forms Active?", Society of Biological Psychiatry, vol. 47, 2000, pp. 325-331.
Lorberbaum et al., "Safety Concerns of TMS", Transcranial Magnetic Stimulation in Neuropsychiatry, 2000, pp. 141-161.
Nahas et al., "Left Prefrontal Transcranial Magnetic Stimulation (TMS) Treatment of Depression in Bipolar Affective Disorder: A Pilot Study of Acute Safety and Efficacy", Bipolar Disorders, vol. 5, 2003, pp. 40-47.
Nahas et al., "Unilateral Left Prefrontal Transcranial Magnetic Stimulation (TMS) Produces Intensity-Dependent Bilateral Effects as Measured by Interleaved BOLD fMRI", Society of Biological Psychiatry, vol. 50, 2001, pp. 712-720.
Pridmore, Saxby, "Substitution of Rapid Transcranial Magnetic Stimulation Treatments for Electroconvulsive Therapy Treatments in a Course of Electroconvulsive Therapy", Depression and Anxiety, vol. 12, 2000, pp. 118-123.
Ruohonen et al., "Electroencephalography Combined with TMS", BioMag Laboratory, Helsinki University Central Hospital, http://www.biomag.helsinki.fi/tms/TMSEEG.html, Oct. 6, 1999, 22 pages.
Wassermann, Eric M., "Repetitive Transcranial Magnetic Stimulation: An Introduction and Overview", CNS Spectrums, The International Journal of Neuropsychiatric Medicine, Jan. 1997, 7 pages.

* cited by examiner

FERROFLUIDIC COOLING AND ACOUSTICAL NOISE REDUCTION IN MAGNETIC STIMULATORS

REFERENCE TO RELATED APPLICATION

This application is a continuation of U.S. patent application Ser. No. 11/130,657, filed May 17, 2005, now U.S. Pat. No. 7,396,326, issued Jul. 8, 2008, entitled "FERROFLUIDIC COOLING AND ACOUSTICAL NOISE REDUCTION IN MAGNETIC STIMULATORS".

FIELD OF THE INVENTION

The invention relates to the field of magnetic stimulation. Specifically, the invention relates to acoustically insulating a magnetic stimulation device. In addition, the invention relates to acoustically insulating such a magnetic stimulation device while cooling the device.

BACKGROUND OF THE INVENTION

Magnetic devices are used in many applications, such as in magnetic stimulation devices, speakers and so forth. Magnetic devices tend to generate heat because of resistive losses in the coil(s) that generate magnetic fields(s), and the amount of heat generated is proportional to the amount of power consumed by the device. Thus, high-voltage magnetic devices that consume large amounts of power, such as those used in magnetic stimulation therapy, can become very hot when in operation. The environment in which the magnetic device operates—or the operating characteristics of the device itself—may dictate that the device operate under a certain temperature threshold. For example, in magnetic stimulation therapy, the temperature of a magnetic stimulation device used to generate a therapeutic magnetic field should be kept below approximately 41.5° C. to stay within certain regulatory requirements (e.g., FDA guidelines). If a magnetic stimulation device is to be operated at temperatures exceeding 41.5° C., such regulatory requirements dictate that the device manufacturer and/or health practitioner must meet additional guidelines to prove that operation of the device is safe. These additional requirements increase complexity of operation and overall cost, and are best avoided when possible.

Conventionally, a magnetic stimulation device used for such therapy is used until it reaches a threshold temperature, and then the therapy is temporarily halted until the stimulation device cools. Such an arrangement therefore adds to the time required to perform a treatment, which is undesirable for both the patient and the health practitioner. Alternatively, a second magnetic stimulation device may need to be used (i.e., swapped with the first device when the first device reaches the threshold temperature) so as to continue the therapy without interruption while the first, overheated stimulation device cools. This arrangement is also undesirable because of the added expense associated with the purchase and maintenance of an additional magnetic stimulation device. Furthermore, additional time is required of the patient and health practitioner, as the second magnetic device will need to be set-up and/or calibrated to perform magnetic stimulation therapy on the patient. Because the set-up and/or calibration steps provide opportunities for operator error, requiring the operator to perform such steps multiple times may decrease the overall safety level of the treatment.

Conventional cooling solutions typically involve the use of air or fluid cooling mechanisms. An air cooling mechanism may involve a fan that rapidly circulates cooled or room temperature air past the magnetic device. A fluid cooling mechanism may involve the circulation of a cool fluid past the magnetic device, where the fluid cools the device and is heated in the process, and then to a cooling mechanism, after which the fluid is returned to the magnetic device. Both mechanisms have several drawbacks. For example, both mechanisms require additional moving parts (e.g., fans, cooling mechanisms such as a refrigeration or heat exchange unit, etc.), which add to the cost and complexity of the magnetic device. Furthermore, the additional moving parts add to the potential for a device malfunction.

An additional consideration of magnetic devices is acoustical noise generated by the magnetic coil of a magnetic device as the coil is energized. For example, when the coil is energized, it creates a strong magnetic field that, in many applications, rapidly changes in intensity. The changing magnetic field causes windings of the coil to experience hoop stresses that intermittently stress the windings, which causes a sharp acoustic click.

Such noise is especially pronounced in magnetic stimulation devices, as the therapeutic magnetic fields are created by pulsing the stimulation device's coil. Such noise is problematic for patients, as the stimulation device is typically located in close proximity to the patient's head, and therefore the noise from the stimulation device may be uncomfortable. In addition, a health practitioner who is repeatedly exposed to such noise may be adversely affected. A conventional solution, placing earplugs in the patient's ears, is undesirable because it is an additional step to perform in the therapeutic process and does not solve the problem of the noise caused by the device in the treatment facility (e.g., physician's office, hospital, etc.). In addition, the use of earplugs is undesirable because some psychiatric or young patients may be uncooperative, and therefore the use of earplugs unnecessarily complicates the procedure.

Thus, a conventional solution for the reduction of acoustical noise is the placement of noise reduction material around all or part of a magnetic device. Alternatively, a chamber containing a partial vacuum may be formed around the magnetic device, because a partial vacuum contains very few particles that may propagate a mechanical (sound) wave. However, such noise reduction techniques have the disadvantage of adversely affecting heat transfer for cooling. For example, the best noise reduction materials are fabricated to contain air pockets that do not transfer noise well. However, such air pockets also have the characteristic being poor conductors of heat. The same is true to an even greater extent in the case of a vacuum. Thus, if such a noise reduction technique is used, the magnetic stimulation device cannot be adequately cooled. Attempting to mitigate such a dilemma by placing acoustical material, or forming a partial vacuum, around a cooling system that is itself arranged around a magnetic device is undesirable because of the added size, cost and complexity of the resulting device.

Conventionally, ferrofluids have been used to cool audio speaker systems, which is a lower voltage application when compared to a magnetic stimulation device or other high voltage magnetic device. A ferrofluid is a fluid with suspended ferromagnetic particles. The ferromagnetic particles can be influenced by the magnetic field created by the speaker so as to enhance fluid convection between the speaker and a heat sink to cool the speaker. An additional benefit of ferrofluids is that they can be used to cool a device while still performing noise reduction, because a ferrofluid typically does not support shear waves. Furthermore, a mismatch in sound velocity may also cause the reflection of some of the sound waves.

Unfortunately, even the ferrofluid solution used in connection with speakers has disadvantages that may render it unsuitable for use with high voltage magnetic devices, such as a magnetic stimulation device. For example, the ferrofluid used in connection with speaker cooling, while a dielectric when exposed to normal speaker-level voltages, may be unable to maintain dielectric isolation at the higher voltage levels used in connection with a magnetic stimulation device. As a result, arcing or other problems may occur.

Therefore, what is needed is a ferrofluidic cooling apparatus, system and method for high voltage applications. More particularly, what is needed is an apparatus, system and method for convectively circulating a ferrofluid to cool a high voltage magnetic device. Even more particularly, what is needed is an apparatus, system and method of using a ferrofluid to cool such a high voltage magnetic device while also mitigating acoustical noise.

SUMMARY OF THE INVENTION

In view of the foregoing shortcomings and drawbacks, an apparatus, system and method for acoustically insulating a magnetic stimulation device is described. According to an embodiment, a ferrofluid chamber has a housing that is adapted to be coupled to a component that generates a magnetic field. The housing may be disposed around the component so as to insulate a noise-producing region of the component. A sound absorbing device may be disposed around the housing to reduce noise transmission. The magnetic field may be of sufficient strength to stimulate anatomical tissue. In addition, a ferrofluid may be disposed within the housing for cooling the component.

DETAILED DESCRIPTION OF ILLUSTRATIVE EMBODIMENTS

Figure 1:
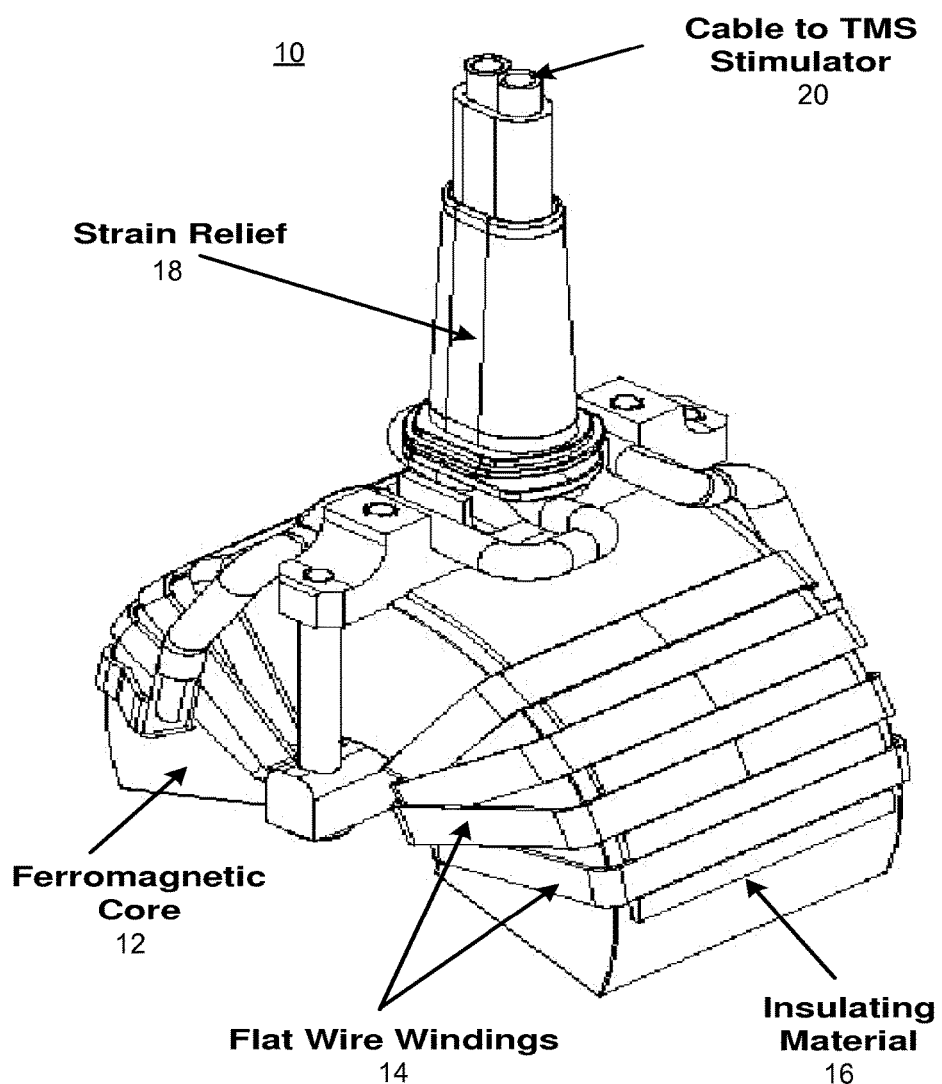
FIG. 1 is a diagram illustrating an example magnetic stimulation device in which aspects of the invention may be implemented.

The subject matter of the present invention is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Magnetic Device Overview

As is well known to those skilled in the art, the magnitude of an electric field induced on a conductor is proportional to the rate of change of magnetic flux density across the conductor. When an electric field is induced in a conductor, the electric field creates a corresponding current flow in the conductor. The current flow is in the same direction of the electric field vector at a given point. The peak electric field occurs when the time rate of change of the magnetic flux density is the greatest and diminishes at other times. During a magnetic pulse, the current flows in a direction that tends to preserve the magnetic field (i.e., Lenz's Law).

As may be appreciated, various devices may take advantage of the above principles to induce an electric field, and such devices may be used in a variety of applications. For example, magnetic devices may be used for electrical stimulation of the anatomy, and the like. While the discussion herein focuses on magnetic devices that are used in connection with magnetic stimulation of anatomical tissue, it will be appreciated that such discussion is so limited solely for purposes of explanation and clarity. Thus, it will be understood that an embodiment is equally applicable to any application of a magnetic device in any field of endeavor. Thus, the present discussion of magnetic devices should not be construed as limiting embodiments of the invention to medical or other applications.

Therefore, and turning now to the context of electrical stimulation of the anatomy, certain parts of the anatomy (e.g., nerves, tissue, muscle, brain) act as a conductor and carry electric current when an electric field is applied. The electric field may be applied to these parts of the anatomy transcutaneously by applying a time varying (e.g., pulsed) magnetic field to the portion of the body. For example, in the context of TMS, a time-varying magnetic field may be applied across the skull to create an electric field in the brain tissue, which produces a current. If the induced current is of sufficient density, neuron action potential may be reduced to the extent that the membrane sodium channels open and an action potential response is created. An impulse of current is then propagated along the axon membrane that transmits information to other neurons via modulation of neurotransmitters. Such magnetic stimulation has been shown to acutely affect glucose metabolism and local blood flow in cortical tissue. In the case of major depressive disorder, neurotransmitter dysregulation and abnormal glucose metabolism in the prefrontal cortex and the connected limbic structures may be a likely pathophysiology. Repeated application of magnetic stimulation to the prefrontal cortex may produce chronic changes in neurotransmitter concentrations and metabolism so that depression is alleviated.

In a similar fashion, non-cortical neurons (e.g., cranial nerves, peripheral nerves, sensory nerves) may also be stimulated by an induced electric field. Techniques have been developed to intentionally stimulate peripheral nerves to diagnose neuropathologies by observing response times and conduction velocities in response to a pulsed magnetic field induced stimulus. Discomfort and/or pain may result if the induced electric field applied to a peripheral or cranial nerve is very intense or focused on a small area of such a nerve. This discomfort may be diminished by intentionally over-stimulating the sensory nerves in the affected nerve bundle so that they can no longer respond to external pain stimuli, or by reducing the intensity and focus of the induced electric field that is causing the pain sensation.

As noted above, it should be appreciated that transcutaneous magnetic stimulation is not limited to treatment of depression. In addition to depression, the transcutaneous magnetic stimulation methods and apparatus of the invention may be used to treat a patient such as a human suffering from epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (e.g., panic disorder with and without agoraphobia, social phobia also known as social anxiety disorder, acute stress disorder and generalized anxiety disorder), post-traumatic stress disorder (one of the anxiety disorders in DSM), obsessive compulsive disorder (also one of the anxiety disorders in DSM), pain (such as, for example, migraine and trigeminal neuralgia, as well as chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (e.g., dependence, abuse and withdrawal diagnoses for alcohol, cocaine, amphetamine, caffeine, nicotine, cannabis and the like), spinal cord injury and regeneration/rehabilitation, stroke, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, and/or eating disorders (such as bulimia, anorexia and binge eating).

Example Magnetic Stimulation Device

A ferromagnetic core may be used in connection with a magnetic device to produce a magnetic field. In some embodiments, such a magnetic field may be for purposes of carrying out transcutaneous magnetic stimulation such as, for example, Transcranial Magnetic Stimulation (TMS), Repetitive TMS (rTMS), Magnetic Seizure Therapy (MST), reduction of peripheral nerve discomfort and so forth. Again, although some of the examples that follow may be discussed in connection with TMS and rTMS embodiments for the purposes of explanation and clarity, any type of transcutaneous magnetic stimulation, including all of those listed above, may be performed according to an embodiment of the invention. In addition, and as noted above, embodiments of the invention are not limited to transcutaneous magnetic stimulation, as an embodiment may be used in connection with magnetic devices that generate a magnetic field for any purpose.

Furthermore, embodiments of the invention are not limited to the use of ferromagnetic core magnetic stimulation devices, as other core materials may be used such as, for example, air. The discussion herein therefore describes a ferromagnetic core magnetic stimulation device solely for purposes of explanation and clarity. In an embodiment, a ferromagnetic core may be approximately hemispherical, and in another embodiment the ferromagnetic core may include a highly saturable magnetic material having a magnetic saturation of at least 0.5 Tesla. In some embodiments, a ferromagnetic core may be shaped to optimize the magnetic field distribution in the treatment area. Treatment areas for other forms of treatment (e.g., reduction of discomfort in peripheral nerves, etc.) may be more or less deep than is the case for TMS.

FIG. 1 illustrates an example magnetic device 10, or "coil," that may be used in connection with an embodiment of the invention. Device 10 comprises a ferromagnetic core 12 surrounded by windings 14. An insulative material 16 may be interposed between core 12 and windings 14. Device 10 also includes a cable 20 for connecting device 10 to a control system (not shown in FIG. 1 for clarity). Cable 20 may be covered by a housing 18 for protection and strain relief.

Ferromagnetic core 12 can be fabricated from various ferromagnetic materials such as, for example, 3% grain oriented silicon steel or vanadium permendur (also known as supermendur). The material is chosen to have, for example, a high saturation level, a sharp-knee B-H curve (i.e., quickly switches from saturated to non-saturated states), low eddy current losses, and a practical cost. The core material may be fabricated into many electrically isolated layers to minimize eddy current losses. The orientation of the lamination may be such as to disrupt the eddy currents (i.e., perpendicular to the direction of induced current flow whenever possible). Also, if the material has a grain orientation, it may be directed parallel to the induced magnetic flux. In one embodiment, the ferromagnetic core is according to U.S. Pat. Nos. 6,132,361 and 5,725,471, each of which is hereby incorporated by reference in their entireties.

In one embodiment, patient treatment typically includes applying a magnetic field to the patient using a coil constructed with an approximately hemispherical ferromagnetic core. The strength of the field and switching rate is sufficient to produce stimulation of the target area in a manner that is appropriate to the type of treatment being administered. As noted above, the generation of a magnetic field having the approximate strength for therapeutic treatment or other purposes also generates heat and noise. Therefore, an embodiment that provides an apparatus, system and method for mitigating such heat and/or noise using a ferrofluid is discussed below.

Ferrofluidic Convection and Cooling

Generally, a ferrofluid is a suspension of small magnetic particles that may be, for example, approximately 10 nm in size. Such a small particle size may be selected to assure that settling of the particles does not occur during a time period that is appropriate for an application in which the ferrofluid is used. In addition, one or more surfactants may be used to ensure continued suspension of the magnetic particles in the fluid, which may be, for example, oil, water, etc. Each particle may have a permanent magnetic moment, and may be comprised from magnetic materials such as, for example, iron oxide compounds or the like. In the absence of an external magnetic field, the magnetic moments of the individual particles within the ferrofluid are not aligned with each other. When a magnetic field is applied, the magnetic moments align with the applied magnetic field. This alignment often is called "superparamagnetic" as the fluid behaves as a paramagnet with magnetic moments that are the size of the individual magnetic particles.

It will be appreciated that an increase in temperature of a ferrofluid decreases its magnetization in an applied field. For example, at higher temperatures, the saturation moment of a ferrofluid, as well as its initial susceptibility, are reduced. The relationship between the magnetization of a ferrofluid and an applied magnetic field is called the Langevin function, which is known to those of skill in the art.

Natural convection is a phenomenon caused by the change in volume of liquid with temperature. Hot fluids are less dense, and therefore a fluid exposed to a heat source will expand and rise. Cool fluid distant from a heat source will move to replace the hot fluid. In this way, heat is mechanically transported away from a heat source.

In the case of ferrofluid convection, a ferrofluid is placed in a magnetic field gradient where the magnetic field is greatest. As noted above, a cool ferrofluid has a higher magnetic susceptibility than a hot ferrofluid and therefore is preferentially drawn to the areas of greatest magnetic field. In an embodiment, the area of the cool ferrofluid greatest magnetic field may be proximate a magnetic device (e.g., a magnetic stimulation device, or the like) when such a magnetic device is in operation. Therefore, ferrofluid that is proximate the magnetic device may be heated, which reduces the ferrofluid's magnetic susceptibility and also causes the ferrofluid to expand in volume. As a result, cool ferrofluid (e.g., ferrofluid that is further away from the magnetic device), which has a higher magnetic susceptibility and is more dense, is drawn to the magnetic device. Thus, it will be appreciated that magnetic and thermal convection of the ferrofluid may be established by the increasing and decreasing of the magnetic susceptibility and volume of the ferrofluid. Details relating to the fabrication of ferrofluid-filled chambers is assumed to be known to those of skill in the art, and such details are therefore omitted herein for clarity.

In addition, ferrofluids may be used to reduce unwanted noise in solenoids and other devices. This is because a ferrofluid is not a good supporter of transverse sound waves. Also, an interface between a ferrofluid and an adjacent object (e.g., a magnetic device or the like) may reduce noise produced by the magnetic device. This is because of the difference of sound velocities at such an interface, as is known to one of skill in the art. Furthermore, the ferrofluid may provide vibrational damping. Thus, it will be appreciated that a ferrofluid that is being used to cool a magnetic device may also reduce noise produced by such a magnetic device. It will be further appreciated that a ferrofluid that is being used to cool a magnetic device may, for example, be used in connection with other methods of sound absorption. For example, sound absorbing material may be used to augment the sound-reducing abilities of the ferrofluid.

An embodiment provides a chamber containing a ferrofluid. The ferrofluid within the chamber may be used to cool a magnetic device substantially around which the chamber may be disposed. For example, a magnetic field created by the magnetic device may induce magnetic convection of the ferrofluid as discussed above. In addition, the heat generated by the magnetic device may induce thermal convection.

In one embodiment, a heat exchanger may be coupled to the chamber to cool the ferrofuid, thereby further enabling cooling of the magnetic device as the ferrofluid circulates between the device, where the ferrofluid is heated, and the heat exchanger, where the ferrofluid is cooled. Sound reduction may also be affected by the ferrofluid, as in one embodiment the chamber may be disposed around the magnetic stimulation device to substantially enclose a sound-producing region of the device. In an embodiment, properties of the ferrofluid may be selected so as to enhance its magnetic, thermal and/or sound-mitigating properties.

While an embodiment discussed herein relates to Magnetic Seizure Therapy (MST) and Transcranial Magnetic Stimulation (TMS) for purposes of explanation and clarity, it will be appreciated that an embodiment may be employed in connection with any type of high-voltage magnetic device that is used for any purpose.

Figure 2:
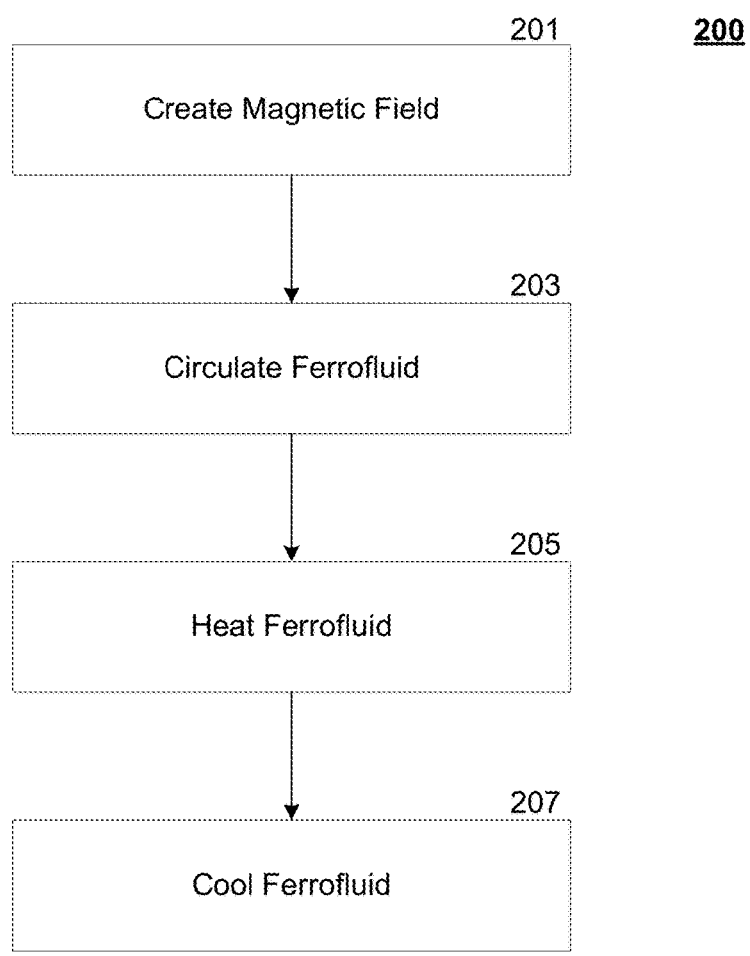
FIG. 2 is a flowchart illustrating an example method of cooling a magnetic device in accordance with an embodiment of the invention.

Turning now to FIG. 2, a flowchart illustrating a method of cooling a magnetic device is provided. Cooling method 200 illustrated in FIG. 2 begins, for example, at step 201 where a magnetic field is created. Such a magnetic field may be created by, for example, magnetic device 10 as discussed above in connection with FIG. 1, or by any other type of magnetic device. In an embodiment, the magnetic field created at step 201 may be of sufficient strength to stimulate anatomical tissue. Even in such an embodiment, however, the magnetic field may be used for an application other than tissue stimulation, even though the magnetic field is of sufficient strength to do so. In an embodiment involving TMS, for example, magnetic device 10 may operate using voltage levels of approximately 1,500 V or more.

At step 203, a ferrofluid is circulated. It will be appreciated that a ferrofluid may be contained within a chamber, as will be discussed below in connection with FIGS. 3-6. The ferrofluid may be circulated by way of magnetic convection, as was discussed in detail above, induced by the magnetic field created by, for example, magnetic device 10. In an embodiment, one on more magnetic field-creating devices may create one or more magnetic fields to induce magnetic convection such as, for example, in the example configuration discussed below in connection with FIG. 5. Moreover, additional components may be used to mechanically circulate the ferrofluid, as will be discussed below in connection with the example configuration of FIG. 6.

At step 205, the ferrofluid is heated. Such heating may take place, for example, proximate magnetic device 10. Such heating may occur due to the heating of such device 10 while device 10 is in operation, as was discussed above. At step 207, the ferrofluid is cooled. Such cooling may take place due to, for example, heat loss facilitated by a heat exchanger such as a heat sink, refrigeration unit or the like. Alternatively, such cooling may take place without the assistance of a heat exchanger. It will be appreciated that the heating of step 205 and the cooling of step 207 may facilitate thermal convection of the ferrofluid, as was discussed above. Such thermal convection may, in an embodiment, assist the magnetic convection of the ferrofluid discussed above in connection with step 203.

Figure 3:
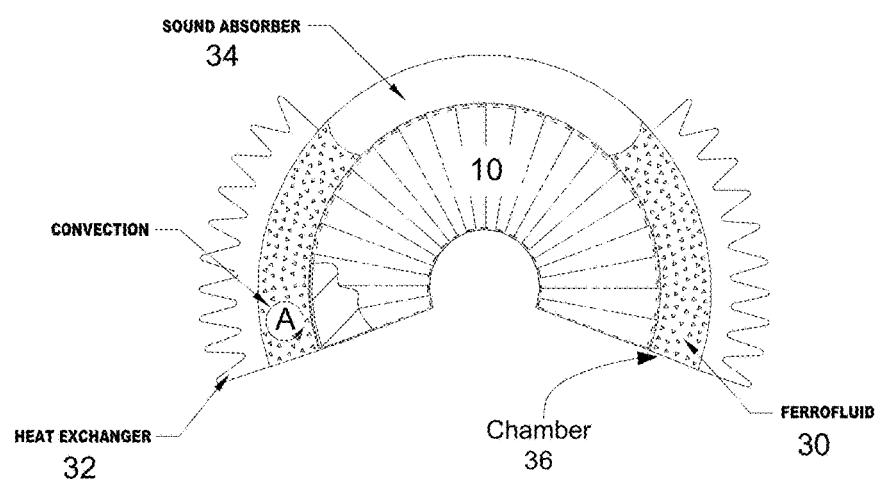
FIGS. 3-6 are diagrams illustrating example configurations involving ferrofluidic cooling of a magnetic device in accordance with an embodiment of the invention.
Figure 4:
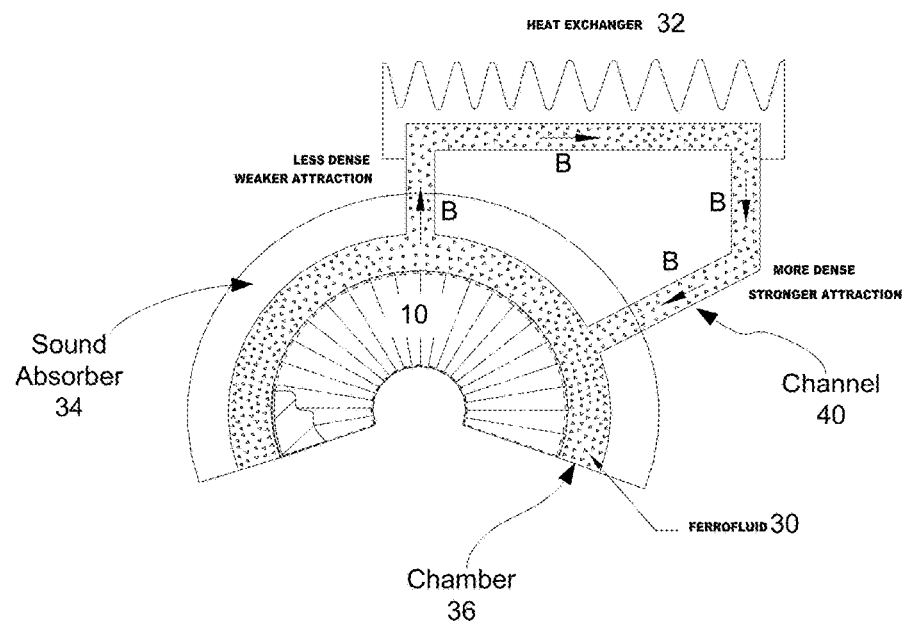

FIG. 3 illustrates an example implementation of ferrofluidic cooling of a magnetic device in accordance with an embodiment. Although magnetic device 10 is illustrated as having a ferromagnetic core in FIG. 3, it will be appreciated that magnetic device 10 may be any type of device that is capable of generating a magnetic field.

As can be seen in FIG. 3, chamber 36 is disposed around device 10. Contained within chamber 36 is ferrofluid 30, and disposed around chamber 36 is heat exchanger 32. It will be appreciated that heat exchanger 32 may be any means for cooling ferrofluid 30 including, but not limited to, a heat sink as illustrated in connection with FIG. 3. In addition, in some embodiments additional components may be used in connection with heat exchanger 32 such as, for example, a fan, a refrigeration unit or the like. Furthermore, it will be appreciated that an embodiment may require no heat exchanger 32, as ferrofluid 30 may be cooled by air surrounding chamber 36, for example.

It can be seen in FIG. 3 that sound absorber 34 is also disposed around device 10 for noise-reduction purposes. Sound absorber 34 may be any means for reducing sound transmission, such as for example sound-absorbing material, active noise-reduction equipment, and so forth. Thus, it will be appreciated that in some embodiments the noise reducing properties of ferrofluid 30 may be augmented with one or more sound reduction techniques.

Convection (i.e., magnetic and/or thermal convection) of ferrofluid 30 is enabled as discussed above, and is represented by direction arrow A. Thus, it can be appreciated that, in an embodiment, ferrofluid 30 that is proximate device 10 while device 10 is in operation and therefore generating heat is also heated. In addition, ferrofluid 30 may be attracted to device 10 because of a magnetic field generated by device 10 (not shown in FIG. 3 for clarity). As noted above, the volume of a heated ferrofluid 30 increases while its magnetic susceptibility decreases. Therefore, ferrofluid 30 that is proximate heat exchanger 32 may be cooler relative to ferrofluid 30 located proximate device 10, and as a result may be denser and may experience a stronger magnetic pull to device 10. As may be appreciated, the heating and cooling of ferrofluid 30, as well as its increasing and decreasing magnetic susceptibility, causes ferrofluid 30 to experience thermal and magnetic convection.

It should be appreciated that the example configuration depicted in FIG. 3 is merely representative of any number of configurations that may be implemented in connection with an embodiment. To illustrate this point, we turn now to FIG. 4, which depicts another example implementation according to an embodiment.

In FIG. 4, device 10 is again illustrated with chamber 36 disposed around device 10. Chamber 36 further has channel 40 formed therein to convey ferrofluid 30 to and from heat exchanger 32. The movement of ferrofluid 30 to and from heat exchanger 32 is represented by direction arrow B. It will be appreciated that heat exchanger may be as described above in connection with FIG. 3. The configuration illustrated in FIG. 4 differs from that illustrated in FIG. 3 in that sound absorber 34 is disposed around chamber 36, rather than being used in place of chamber 36 in certain locations.

Figure 5:
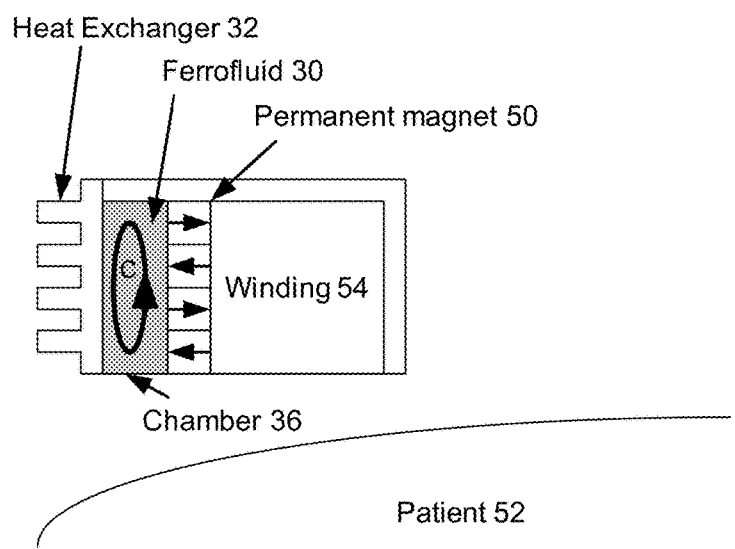

FIG. 5 illustrates another example configuration according to an embodiment. Specifically, FIG. 5 illustrates a winding 54 that may be part of magnetic device 10 (wherein device 10 is not illustrated in its entirety in FIG. 5 for clarity) that may be used in, for example, a medical application such as MST, TMS or the like. As may be appreciated, winding 54 may be energized to cause device 10 to generate a magnetic field, which may be used to treat patient 52 and/or drive magnetic convection of ferrofluid 30, as indicated by directions arrow C. In addition, permanent magnet 50 may be present to induce continuous or near-continuous convection of ferrofluid 30 (also represented by direction arrow C). Such a configuration, in an embodiment, serves to keep ferrofluid 30 within chamber 36 to remain relatively cool at all times, as ferrofluid 30 will be constantly circulating past heat exchanger 32. It will be appreciated that in some embodiments convection of ferrofluid 30 induced by permanent magnet 50 and convection of ferrofluid 30 induced by winding 54 may be additive. In other words, ferrofluid 30 may experience more powerful convection when winding 54 is energized, for example.

Figure 6:
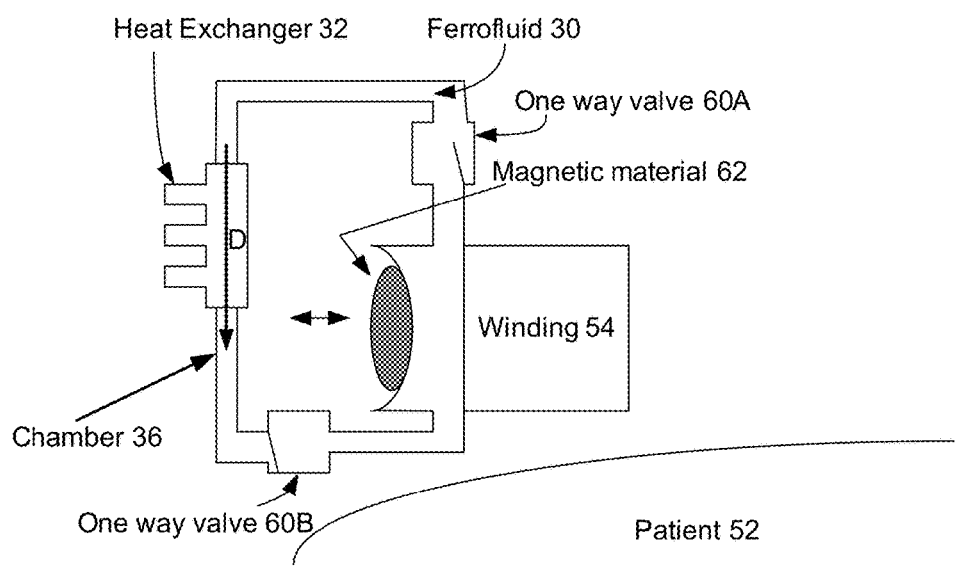

Turning now to FIG. 6, another example configuration according to an embodiment is illustrated. In FIG. 6, chamber 36 is disposed proximate winding 54 and is at least partially filled with ferrofluid 30. Magnetic material 62 may be positioned proximate chamber 36 and winding 54. As may be appreciated, magnetic material 62 may be attracted to (or repelled from) winding 54, depending on, for example, a magnetic field generated by winding 54 and/or device 10 (not shown in FIG. 6 for clarity). In an embodiment, magnetic material 62 may be mounted on, for example, a flexible membrane or the like to permit magnetic material 62 to move within a desired area to cause ferrofluid 30 to circulate throughout chamber 36 as indicated by direction arrow D. It will be appreciated that any such mechanical circulation induced by magnetic material 62 may be in addition to or in place of any of the above-described thermal and/or magnetic convection of ferrofluid 30 that may be caused by a magnetic field cased by winding 54.

In addition, one-way valves 60A-B may be present to facilitate enhanced circulation of ferrofluid 30. For example, magnetic material 62 may cause ferrofluid 30 to flow in the direction indicated by arrow D when attracted to winding 54, but may cause ferrofluid 30 to flow in an opposite direction when repelled from winding 54. Thus, one or more one-way valves 60A-B may be operatively coupled to chamber 36 to ensure that ferrofluid 30 only flows in the direction indicated by arrow D. It should be appreciated that any technique may be used to ensure such directional flow of ferrofluid 30, if any is used at all, and any such apparatus is equally consistent with an embodiment.

Therefore, it will be appreciated that magnetic material 62 acts as a pumping mechanism for driving the circulation of ferrofluid 30. Alternate embodiments may use other such pumping mechanisms, and such embodiments are in no way limited to the use of magnetic material 62, which is presented herein merely as an illustrative example. For example, a fluid pump may be operatively coupled to chamber 36 to circulate ferrofluid 30, and such a configuration would remain consistent with an embodiment. In addition, such a fluid pump (or a second fluid pump) may also circulate an additional, non-ferrofluid for additional cooling or other purposes. Thus, any type of pumping mechanism may be employed to circulate ferrofluid 30, and any such pumping mechanism may operate to augment or replace the aforementioned magnetic and/or thermal convection of ferrofluid 30.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention.

What is claimed:

1. A magnetic stimulation system providing acoustical noise reduction, the magnetic stimulation system comprising:
    a component for generating a magnetic field having a sufficient strength to stimulate anatomical tissue; and
    a chamber coupled to and substantially surrounding the component; and
    a ferrofluid disposed in the chamber, wherein the magnetic stimulation system is configured to magnetically induce convection of the ferrofluid in the chamber, wherein the chamber is disposed around the component, wherein a portion of the component is left exposed by the chamber and the chamber substantially encloses an acoustic noise-producing region of the component, the ferrofluid being configured to reduce noise produced by the component, and wherein the component and the chamber are disposed within a housing configured to conform to a head of a human subject.

2. The system of claim 1, further comprising a heat exchanger coupled to the chamber.

3. The system of claim 2, wherein the ferrofluid is resistant to shear sound waves.

4. The system of claim 2, wherein the ferrofluid in the chamber and the magnetic stimulation system form a first noise-attenuating interface.

5. The system of claim 2, wherein the ferrofluid in the chamber and the heat exchanger form a second noise-attenuating interface.

6. The system of claim 2, wherein the heat exchanger is configured to cool the ferrofluid.

7. The system of claim 6, wherein the heat exchanger is a heat sink.

8. The system of claim 2, further comprising a pumping mechanism configured to circulate the ferrofluid between the component and the heat exchanger.

9. The system of claim 8, wherein the pumping mechanism is activated by a pulsing magnetic field causing circulation of the ferrofluid in a first direction when in the presence of the magnetic field.

10. The system of claim 9, further comprising a valve configured to prevent the ferrofluid from circulating in a second direction.

11. The system of claim 1, further comprising a sound absorber disposed around the component, the sound absorber being configured to enclose a portion of the acoustic noise-producing region of the component.

12. The system of claim 1, further comprising a sound absorber disposed around the chamber, the sound absorber being configured to reduce noise transmission.

13. The system of claim 1, wherein the component is a coil.

14. The system of claim 13, wherein the coil has a ferromagnetic core.

15. The system of claim 13, wherein the coil has an air core.

16. The system of claim 1, wherein the component is configured to stimulate human brain tissue in connection with transcranial magnetic stimulation.

17. The system of claim 1, wherein the magnetic field is a first magnetic field, and further comprising a permanent magnet to create a second magnetic field, wherein the ferrofluid experiences magnetic convection when exposed to the second magnetic field.

18. The system of claim 1, further comprising a magnetic material configured to cause circulation of the ferrofluid when in the presence of the magnetic field.

19. A ferrofluid chamber, comprising:
a housing configured to be coupled to a component, the component being configured to provide magnetic stimulation, wherein the housing is configured to conform to a head of a human subject; and
a ferrofluid disposed in the housing that experiences convection when exposed to a magnetic field, wherein the housing is disposed around the component and wherein the housing exposes a portion of the component, the component being configured to generate a magnetic field having a sufficient strength to stimulate anatomical tissue, wherein the chamber substantially encloses an acoustic noise-producing region of the component, and wherein the ferrofluid is configured to reduce noise produced by the component.

20. The chamber of claim 19, wherein the ferrofluid contained within the chamber and the component form a first noise-attenuating interface.

21. The chamber of claim 19, wherein the ferrofluid contained within the chamber and a heat exchanger form a second noise-attenuating interface.

22. The chamber of claim 19, wherein the ferrofluid is resistant to shear sound waves.

23. The chamber of claim 19, further comprising a sound absorber disposed around the component, the sound absorber being configured to enclose a portion of the acoustic noise-producing region of the component.

24. The chamber of claim 19, further comprising a sound absorber disposed around the chamber, the sound absorber being configured to reduce noise transmission.

25. The chamber of claim 19, further comprising a heat exchanger coupled to the housing for cooling the ferrofluid.

26. The chamber of claim 25, wherein the heat exchanger is a heat sink.

27. The chamber of claim 25, further comprising a pumping mechanism to cause the ferrofluid to circulate between the component and the heat exchanger.

28. The chamber of claim 27, wherein the pumping mechanism is a magnetic material for causing circulation in the presence of the magnetic field.

29. The chamber of claim 19, wherein the component is a coil.

30. The chamber of claim 29, wherein the coil has a ferromagnetic core.

31. The chamber of claim 29, wherein the coil has an air core.

32. The chamber of claim 19, wherein the component is configured to stimulate human brain tissue in connection with transcranial magnetic stimulation.

33. The chamber of claim 19, wherein the magnetic field is a first magnetic field, and further comprising a permanent magnet proximate the housing to create a second magnetic field, wherein the ferrofluid experiences magnetic convection when exposed to the second magnetic field.

34. A method of reducing acoustical noise while cooling a magnetic stimulation device, comprising:
creating a magnetic field with the magnetic stimulation device, wherein the magnetic field is of sufficient strength to stimulate anatomical tissue;
circulating a ferrofluid by inducing convection with the magnetic field, wherein the circulating ferrofluid cools the magnetic stimulation device, the ferrofluid being circulated in a housing disposed around the magnetic stimulation device, wherein a portion of the magnetic stimulation device is left exposed by the housing, wherein the housing substantially encloses a noise-producing region of the magnetic stimulation device, and wherein the housing is configured to conform to a head of a human subject; and
reducing noise produced by the magnetic stimulation device, wherein the noise is reduced by the ferrofluid in the housing.

35. The method of claim 34, further comprising reducing noise transmission by introducing a sound absorber disposed around an acoustic noise-producing region of the magnetic stimulation device, the sound absorber being configured to enclose a portion of the acoustic noise-producing region.

36. The method of claim 34, further comprising reducing noise transmission by introducing a sound absorber disposed around the housing.

* * * * *